United States Patent [19]

Premuzic

[11] Patent Number: 4,780,238

[45] Date of Patent: Oct. 25, 1988

[54] NATURAL CHELATING AGENTS FOR RADIONUCLIDE DECORPORATION

[75] Inventor: Eugene T. Premuzic, East Moriches, N.Y.

[73] Assignee: The United States of America as represented by the United States Department of Energy, Washington, D.C.

[21] Appl. No.: 743,544

[22] Filed: Jun. 11, 1985

Related U.S. Application Data

[63] Continuation-in-part of Ser. No. 526,246, Aug. 25, 1983, abandoned.

[51] Int. Cl.$^4$ .............................. C09K 3/00; G21F 9/04
[52] U.S. Cl. ..................................... 252/184; 252/631; 423/6; 534/11
[58] Field of Search ............... 252/631, 184; 423/6; 534/11

[56] References Cited

U.S. PATENT DOCUMENTS

| | | | |
|---|---|---|---|
| 3,989,595 | 11/1976 | Mateles et al. | 435/68 |
| 4,043,936 | 8/1977 | Francis et al. | 252/631 |
| 4,180,473 | 12/1979 | Maurer et al. | 252/182 |
| 4,227,002 | 10/1980 | Babcock et al. | 252/184 |
| 4,263,403 | 4/1981 | Paschke et al. | 210/601 |
| 4,309,305 | 1/1982 | Weitl et al. | 252/631 |
| 4,320,093 | 3/1982 | Volesky et al. | 423/6 |
| 4,530,763 | 7/1985 | Clyde et al. | 423/3 |
| 4,530,963 | 7/1985 | DeVoe et al. | 210/615 |
| 4,626,416 | 12/1986 | DeVoe et al. | 423/12 |
| 4,666,927 | 5/1987 | Hider et al. | 546/296 |
| 4,698,431 | 10/1987 | Raymond et al. | 546/261 |
| 4,711,718 | 12/1987 | Nelson, Jr. | 210/282 |

OTHER PUBLICATIONS

Premuzic et al., "Production of Chelating Agents by *Pseudomonas Aeruginosa* . . . ", BNL 36301R, 7 pp., *Proceedings of Speciation-85 Seminar* at Oxford, 16-19 Apr. 1985.

Premuzic et al., "Isolation of Natural Chelates for Radionuclide Decorporation", report for DOD, DNA, AFRI, Bethesda, Md. Agreement 82-833 (Mar 1983).

Cox et al. I, *J. of Bacteriology*, Jan. 1979, 357-364 (vol. 137 #1).

Cox et al. II, *Proc. Natl. Acad. Sci. USA*, 78 (#7), 4256-60 (Jul. 1981).

Strandberg et al., *Appl. Environ. Microbiol.*, 41 (#1), 237-45 (1981).

Shiman, R. et al., Biochem 4:2233-2236:1965.

*Primary Examiner*—Edward A. Miller
*Attorney, Agent, or Firm*—Margaret C. Bogosian; James W. Weinberger; Judson R. Hightower

[57] ABSTRACT

This invention relates to the preparation of new, naturally produced chelating agents as well as to the method and resulting chelates of desorbing cultures in a bioavailable form involving Pseudomonas species or other microorganisms. A preferred microorganism is *Pseudomonas aeruginosa* which forms multiple chelates with thorium in the range of molecular weight 100-1,000 and also forms chelates with uranium of molecular weight in the area of 100-1,000 and 1,000-2,000.

4 Claims, No Drawings

NATURAL CHELATING AGENTS FOR RADIONUCLIDE DECORPORATION

BACKGROUND AND GENERAL DESCRIPTION

The United States Government has rights in this invention pursuant to Contract Number DE-AC02-76CH00016, between the United States Department of Energy and Associated Universities Inc.

RELATED APPLICATIONS

This application is a continuation-in-part application of co-pending patent application Ser. No. 526,246 filed Aug. 25, 1983, and now abandoned.

This invention relates to the production of metalbinding compounds useful for biological mining and for decorporation of radionuclides. These metal-binding compounds are complexing and/or chelating agents; compounds containing donor atoms that are capable of combining by complexing or coordinate bonding with a metal atom or atoms to form a cyclic structure, which is called a chelate when the structure is formed by a chelating agent. In the past, a great deal of research has centered around the production of synthetic chelating agents. Numerous chelating agents synthesized chemically are in use today such as the EDTA and DTPA types, sulfhydryl derivatives (BAL and penicillamine) and the tricatecholamide analogs. In addition, selected combinations of these chemically synthesized chelating agents have proven clinically useful; especially the use of BAL and EDTA in the treatment of lead poisoning in children.

Other chelating agents have been prepared by non-challenge biosynthesis. This approach uses chelating agents produced during normal metabolism of microorganisms. This procedure has led to the discovery of naturally occurring iron-binding compounds called siderophores, most important of which is desferrioxamine. The drawback of non-challenge biosynthesis is that it is uncontrolled metabolism and random search for a useful product produced by this metabolism.

The present invention deals with a more orderly and effective method of producing new chelating agents. This method uses challenge biosynthesis for the production of chelating agents that are specific for a particular metal. In this approach, the desired chelating agents are prepared from microorganisms challenged by the metal that the chelating agent is designed to detoxify. This challenge induces the formation of specific or highly selective chelating agents. One tremendous advantage of this approach is that the microorganism pre-selects those compounds most effective to counteract the toxic effects of the challenging metal and thus narrows down the selection to those compounds most satisfactory to the biological requirements of the living organism. There are many advantages to the use of challenge biosynthesis for the development of new chelating agents, including: (1) pre-selection of the most effective chelating agents by the microorganisms; (2) biological compatibility since they are produced under conditions which favor low toxicity; and (3) built-in specificity.

The present invention involves the use of the challenge biosynthetic method to produce new complexing/chelating agents that are useful to detoxify uranium, plutonium, thorium and other toxic metals. The *Pseudomonas aeruginosa* family of organisms is the preferred family of microorganisms to be used in the present invention to produce the new chelating agents because this family is known to elaborate strains resistant to toxic metals. The specific microorganisms most preferred in this application are *P. aeruginosa PAO-*1 (ATCC 15692) and *P. aeruginosa—CSU*. However, other microorganisms may also be used in the challenge biosynthetic approach using thorium, plutonium or uranium as the challenge metals to prepare thorium, plutonium or uranium specific chelating agents. Examples of such microorganisms are set forth in Table 1.

TABLE 1

| List of Cultures | | |
|---|---|---|
| 1. *Aspergillus niger* | ATCC | 34467 |
| 2. *Actinomyces humiferus* | ATCC | 25174 |
| 3. *Azotobacter vinelandii* | ATCC | 7496 |
| 4. *A. vinelandii* | ATCC | 9104 |
| 5. *Micrococcus luteus* | ATCC | 15176 |
| 6. *M. luteus* | ATCC | 15932 |
| 7. *Mycobacterium phlei* | ATCC | 354 |
| 8. *M. phlei* | ATCC | 10142 |
| 9. *M. phlei* | ATCC | 15610 |
| 10. *Pseudomonas aeruginosa* | ATCC | 14885 |
| 11. *P. aeruginosa* | ATCC | 15522 |
| 12. *P. fluorescens* | ATCC | 11250 |
| 13. *P. fluorescens* | ATCC | 13475 |
| 14. *P. fluorescens* | ATCC | 25289 |
| 15. *Brevibacterium iodinum* | ATCC | 15729 |
| 16. *Pseudomonas sp.* | ATCC | 15165 |
| 17. *Pseudomonas sp.* | ATCC | 15779 |
| 18. *Pseudomonas sp.* | ATCC | 19286 |
| 19. *Pseudomonas sp.* | ATCC | 31155 |
| 20. *Pseudomonas sp.* | ATCC | 17483 |

Workers engaged by industries which are involved in the manufacture and use of radioactive materials or are involved in mining, transportation, production and waste disposal of heavy metals may be subject to metal poisoning; further the effects of the industrial activities may be felt by inhabitants near the facility if there is an equipment malfunction. Thus it is very important to have thorium, uranium, plutonium or other toxic metal chelating agents (desorbents) which are rapid, effective, and non-toxic. These desorbents can be used to decorporate such metals as well as in heavy metal recovery processes.

DETAILED DESCRIPTION OF THE INVENTION

The microorganisms which are useful in the production of the specific chelating agents for uranium, plutonium and thorium are grown under optimum laboratory conditions for the maximum production of sequestering agents for these metals. The cells obtained from batch and/or continuous cultures developed for each metal are harvested and fractionated into intracellular and subcellular fractions. The fractions containing the highest concentrations of the metal, as for example thorium are chemically separated and characterized in terms of major compound classes of natural products responsible for the complexation of the particular metals.

Several different chelating agents with molecular weights (MW) of less than 2,000 are produced by *P. aeruginosa* when challenged by thorium or uranium. In the MW range of 1,000–2,000, there were no thorium complexes found. In the 300–1,000 MW range, four thorium complexes were formed. Likewise, in the 100–300 MW range, four thorium complexes were formed. In cultures grown in the presence of uranium, at least two complexes were generated in the 1,000–2,000 MW range; in the 300–1,000 MW range, four uranium complexes; while in the 300 and less MW range, at least seven complexes were formed.

The present data indicate that several of the new chelating agents possess isoquinoline, catechol, phenol, amino and hydroxamate reactive centers.

Extracts containing these new chelating agents have been tested for their decorporation potential. In vitro mouse liver bioassay and in vivo mouse toxicity tests indicate that their efficiency is comparable to diethylenetriaminepentaacetic acid and desferrioxamine and that they are virtually non-toxic to mice.

A key step in this invention is to grow selected microorganisms under optimum conditions in the presence of the challenge metal. Bioavailability of the metal in the culture medium is influenced by the chemical composition of the medium, solubility and the form of the metal, as well as the complexation of the metal, by both inherent (e.g., medium components) and/or de novo formed complexing agents generated by the microorganisms during the growth phase.

For purposes of this invention, the "bioavailable form" of the metal must satisfy the following conditions:

(1) the metal present in the medium is in a soluble form;

(2) under the growth conditions, the concentration of the metal in the medium is not toxic to the microorganism;

(3) the metal must not be bound by large molecular weight compounds, such as carbohydrates and proteins, which may precipitate out and/or cannot pass through the cell wall;

(4) under the growth conditions, complexation of the metal would prevent formation of insoluble hydroxylated polymers; and (5) if an interaction of the metal with the constituents of the control culture medium does occur, then the product should not be insoluble and precipitate out of the solution.

The initial "insoluble form," such as an insoluble salt of the metal, may be considered as the least bioavailable form relative to the ionic or the complexed form of the metal in solution. Further, plutonium, thorium, uranium, and the transuranic metals are known to form polymers in aqueous solutions within certain pH and concentration ranges. These polymeric forms have a wide range of molecular weights ($<2,000-5,000$) and, in terms of complexation and/or the accessibility to the microorganism, are inert and hence, for the purposes of the present invention, they are by definition not bioavailable.

It is noted that thorium in this invention is used as a surrogate for plutonium, since chelating agents effective for thorium are also generally effective for plutonium.

Growth of bacteria and changes in the medium were monitored by absorption spectroscopy and by direct counts. Thorium or uranium concentration were determined spectroscopically. All supernatants from the culture media were ultrafiltered to remove large molecular weight (greater than 5000 daltons) species and then freeze-dried. The concentrated samples were analyzed by gel-permeation, thin-layer and high pressure liquid chromatography, followed by mass-spectroscopy, ultra-violet analysis, infra-red analysis and HNMR if necessary.

The growth of bacteria in defined medium containing thorium was shown over a range of 0 to 10,000 ppm thorium added as $Th(NO_3)_4$. In the selection of bacteria useful in media containing thorium, it was found that in general the Pseudomonales family of bacteria, embracing Pseudomonas generally and specifically the aeruginosa, fluorescens, and Pseudomonas sp. as well as the bacteria from the Micrococcaceae family embracing S. lutea were found to be useful.

It was noted that in the microorganisms where a metal was added to a defined medium there was a lag of growth of the microorganism. This was measured by differences in the increase in turbidity as a measure of growth. In other words, a fairly common feature of the effects of sub-lethal concentrations of metals on bacteria is a retardation of the onset of growth.

Growth of P. aeruginosa in defined medium containing 0, 1, 10, 100, and 1,000 ppm of thorium added as $Th(NO_3)_4$ was determined. The pH of the medium after addition of 1,000 ppm thorium changed to 6.4 from pH 7. Therefore, the pH of the medium was adjusted to 6.9 with 1 N NaOH. One milliliter of a 24 hr old culture P. aeruginosa grown in nutrient broth was transferred to defined medium containing various concentrations of thorium. Increase in turbidity as a measure of growth was monitored. In general, there was a lag period observed in the control samples primarily due to transfer of inoculum from a nutrient rich medium to a defined medium. However, as the concentration of thorium in the medium increased, the lag period of the organism also increased. At 10,000 ppm thorium concentration, there was an extended lag period followed by reduction in growth. This effect of thorium on bacteria may be due to toxicity or bacteriostatic properties. Cultures grew slowly at first and then at a rate nearly equal to that of the control containing no thorium.

The effect of uranium on growth of P. aeruginosa in citrate medium containing 0, 10, 100, 1,000, and 10,000 ppm of uranium, added as uranyl nitrate, was determined. The results indicate uranium has a stronger inhibitory effect on growth of the organism than thorium at similar concentrations.

In studying the effect of iron on the growth of P. aeruginosa in the presence of thorium or uranium, it was found that the addition of supplemental iron (e.g., 18 ppm) had little or no effect on cultures grown in the presence of thorium, but it had a pronounced effect when added to the uranium culture. In media containing thorium, supplemental iron did not significantly effect the growth of bacteria. This suggests that the traces ($<0.05$ ppm) of iron present in the mineral salts are sufficient to support the growth of the organism when grown in the thorium containing medium. Analogous experiments with uranium have shown that there was an increase in lag period in media without supplemental iron. The addition of supplemental iron to the medium decreased the lag period in the growth of the organism by about twelve hours. These results further indicate that P. aeruginosa when grown under identical conditions behaves differently when grown in the presence of thorium than when grown in the presence of uranium.

EXAMPLE 1

General Experimental Techniques

Culture

Pseudomonas aeruginosa CSU, [Strandberg et al., Applied and Environmental Microbiology, 41, No. 1, 237–245 (1981)] was kindly provided by G. Strandberg, Oak Ridge National Laboratory, TN. P. aeruginosa PAO-1 obtained from American Type Culture Collection (ATCC 15692).

Culture Medium

Nutrient broth (Difco, MI) containing 1% dextrose or defined medium [Aikin et al., *Microbios Letters*, 9, 55-66 (1979)] had the following composition per liter: 0.18 mg $FeSO_4.7H_2O$; 0.035 mg $MgSO_4.7H_2O$; 0.67 g disodium glycerol-2-phosphate hydrate, 0.85 g $KNO_3$; 1.17 g $NH_4NO_3$; 2.0 g glucose; 27.1 g trisodium citrate dihydrate; pH adjusted to 6.8 by addition of citric acid (approx. 2 g).

For ATCC 15692, the following medium was used: 5.4 g sodium succinate hexahydrate; 214 mg $NH_4Cl$; 174 mg $K_2SO_4$; 81.3 mg $MgCl_2 \times 6H_2O$; 0.137 mg $ZnCl_2$; 0.127 mg Mn $Cl_2$; all salts were dissolved in 4 mM potassium phosphate buffered at pH 7.4.

Growth of bacteria was monitored by measuring the absorbance at 600 nm in a Spectronic-20 spectrophotometer. Direct counts of bacteria were determined by acridine orange direct counts (AODC) using epifluorescence microscopy [Hobbie et al., *Appl. Environ. Microbiol.*, 33, 1225-1228 (1977)].

Chemicals

Reagent grade thorium nitrate and uranyl nitrate hexahydrate were purchased from ICN Pharmaceuticals, Plainview, NY and were used without further purification. Arsenazo III was purchased from Aldrich Chemical Co., Milwaukee, WI.

Ultrafiltration

After the removal of bacterial cells by centrifugation, all supernatant liquids were filtered through a Millipore PTG CO 2570 filter, to remove substances with a molecular weight larger than 5000 daltons. This step eliminates the larger molecular weight species, e.g., proteins, carbohydrates and polynuclear products (derived from metal ions) which might interfere in isolation and subsequent biological assays.

Characterization of Natural Products Produced by *P. aeruginosa* in the presence of Thorium and Uranium salts The products generated by *P. aeruginosa* in the presence of thorium or uranium, were derived from the following media:
(1) uninoculated medium containing 0 ppm thorium or uranium;
(2) uninoculated medium containing 100 ppm thorium or uranium;
(3) inoculated medium containing 0 ppm thorium or uranium, harvested at time 0 and at late logarithmic growth; (4) inoculated medium containing 100 ppm of thorium or uranium harvested at time 0 and at late logarithmic growth. The media were all centrifuged at $12,000 \times g$; the supernatants ultra-filtered and stored in sterile containers at 5° C. The chemical composition and properties of the ultrafiltrates were assessed by chromatographic and spectroscopic analyses.

Absorption Spectroscopy

Ultraviolet-visible spectra were obtained with a Beckman Acta-III spectrophotometer. Differences in spectral absorption between culture supernatants with and without metal (thorium or uranium) were obtained from: (1) spectra of maximum growth samples run against a reference of zero growth, and (2) spectra of maximum growth samples containing thorium or uranium against a reference of maximum growth without thorium or uranium. Consequently, it was possible to correct and account for the spectral contributions of the medium as well as that of the culture during growth in the absence of metal.

Fluorescence Spectroscopy

Fluorescence spectra of the ultrafiltrates derived from cultures containing thorium and uranium were obtained with a Perkin-Elmer MPF4 fluorescence spectrophotometer by excitation at 360 nm [Cox et al., *J. Bacteriol.*, 137, No. 1, 357-364 (1979)].

Column Chromatography

The ultrafiltrates from culture media were analyzed by gel permeation chromatography. A column ($1 \times 100$ cm) was packed with polyacrylamide gel (Bio-Rad P-2 super fine grade) and calibrated with compounds of known molecular weight: $NaN_3$, glutathione, and blue dextran. Ultrafiltrates were concentrated by freeze drying. Samples for chromatography were prepared by dissolution of freeze dried material in a minimum amount of water before application to the column. Fractions from elution with deionized water (MilliQ) were monitored at two absorbances, 254 nm and 360 nm.

Thin Layer Chromatography (TLC)

TLC was made on cellulose plates (Brinkman polygram cell 300) and the chromatograms were developed in a mixture of water and isopropanol (1:1, v/v) as the mobile phase. Specific visualization methods and/or reagents (e.g. fluorescence, phenol, and amino groups) were used to detect compounds on the developed chromatograms. The colorimetric test for the detection of thorium and uranium, Arsenazo III, was adapted to TLC, and when used in this manner the detection limit was 10 ppm. Arsenazo III reagent does not react with iron. Thorium and uranium complexes were prepared from citrate, oxalate, glucose, and glucose-2 phosphate and were used as standards concomitantly with unknown samples in the TLC runs. The nitrates of thorium and uranium do not migrate under the prescribed experimental conditions.

High Pressure Liquid Chromatography (HPLC)

Analytical HPLC data were obtained on an IBM LC/9533 liquid chromatograph equipped with an IBM C18 column (No. 8635308). Preparative HPLC data were obtained on an Alltech (No. 6231) C18 preparative column with 50% aqueous methanol as the mobile phase.

Mass Spectroscopy

Mass spectra were obtained on a HP5985 mass spectrometer system which uses electron impact as ion source. Solid samples were introduced directly into the ion source.

Nuclear Magnetic Resonance (NMR)

Proton NMR spectra was obtained on a Varian CFT-20 spectrometer. The solvents used were $D_2O$ and $CDCl_3$.

Effect of Thorium and Uranium Concentrations on the Growth of *P. aeruginosa*

One ml of a 24 hour old culture of *P. aeruginosa* was transfered to a 100 ml defined medium containing 0, 1, 10, 100, and 1000 ppm. Thorium (as $Th(NO_3)_4$). The growth of bacteria was then followed as described earlier. Analogous experiments have been carried out using defined media containing uranium added as uranyl nitrate.

EXAMPLE 2

Photometric Determination of Thorium

Thorium (Th) was determined routinely by a spectrophotometric method. In this method, Arsenazo III (a mixture of 1,8-dihydroxynapthalene, 3,6-disulphonic acid, and 2,7-bis[(azo-2)phenylarsonic acid], an azo dye, was used to react with thorium IV in 9N HCl or 0.1 N $H_2SO_4$. The thorium-Arsenazo III complex formation was rapid (<1 min) at room temperature, and the formed complex had a molar extinction of $1.3 \times 10^5$ at 665 nm. The tested sensitivity of this method was 0.01 ppm for thorium in distilled water (standard 1 cm cell measured at 665 nm). In the routine determinations, samples of culture media containing thorium and nutrients for bacterial growth were mixed by volume with the Arsenazo III reagent in a ratio of 1:5, in order to maintain the pH near 1.5, and thus remove any other complexes, such as those due to the medium. Practical sensitivity of the determination was 0.05 ppm, in culture media containing thorium. Since the culture media were slightly colored, a medium absorption correction was determined and applied to all the measurements under standard conditions. In this method, the solutions used should be free of oxidizing agents ($H_2O_2$, $Cl_2$, $Br_2$, etc.) and reducing agents ($Na_2SO_3$, $Ti^{+3}$) because they decrease the sensitivity. The method was simple and sensitive for routine determinations of thorium as well as uranium.

An additional advantage of the thorium-Arsenazo III complex method is that this complex was stable in a strongly acidic solution in which the thorium-anion complexes of culture-medium components (oxalate, phosphate, sulphate, etc.) were decomposed. The amount of thorium measured by this method represented the total thorium in the solution (i.e., $M_T$).

Arsenazo III containing less than 0.1% calcium was purchased from the Aldrich Chemical Co. Thorium nitrate, purchased from K+K Laboratory, Inc., Plainview, N.Y. (Lot Number 18800), was used to prepare standards without further purification. Deionized water was used for all sample preparations and a Beckman DBG Spectrometer was used for all the spectrophotometric measurements.

Thorium or uranium concentrations in bacterial cell biomass were determined in the following manner. The cells were digested in 7N $HNO_3$ at 80° C. for 24 hr. The acid was evaporated to dryness at 130° C., the residue redissolved in distilled water and thorium or uranium concentrations analyzed by the spectrophotometric method using the Arsenazo III procedure.

EXAMPLE 3

Determination of Thorium by an Ion-Selective Electrode

In contrast to the photometric method, the determination of thorium by an ion-selective electrode is carried out near neutral pH, i.e., within the pH range of culture media.

In this method, thorium is determined indirectly. To a sample solution containing thorium, a known excess of fluoride is added. After the reaction, the unreacted fluoride ion is measured with a fluoride ion specific electrode.

A typical reaction for this process is given by

$$2Th^{4+} + 8F^- + 4L \rightarrow ThL_4 + ThF_4 + 4F^-$$

where L is a complexing agent for thorium with a $K > 10^6$, i.e., larger than that of thorium fluoride. Since thorium forms a thorium-tetra-fluoride complex quantitatively, the concentration of thorium is determined from the difference in the amount of added fluoride and excess fluoride.

Usually, the fluoride ion is determined in a sodium acetate buffer containing a complexing agent CDTA (cyclohexylene dinitrilo tetraacetic acid). However, in this buffer, thorium will also be complexed by CDTA and acetate, and, therefore, the method would not be suitable for the present purposes. A modified procedure has been developed for these routine thorium determinations. In the modified procedure, a triethanolamine buffer solution was used which does not interfere with the indirect determination of thorium. Fluoride samples were measured in plastic cups to avoid absorption by glass. An expanded scale pH meter (Corning Digital 110) was used with an Orion combination fluoride electrode. Sodium fluoride (Reagent ACS grade) was purchased from Allied Chemical Co. Specialty Chemical Division, Morristown, N.J. Triethanolamine was purchased from Fisher Scientific Company.

The prepared samples must have a pH value between 5 and 6 to avoid formation of hydrogen fluoride below pH 5 and also to avoid the generation of thorium polyhydroxo complexes above pH 6. The triethanolamine buffer has a low buffering capacity near pH 5.5 and, hence, requires a large (1 to 10) dilution factor to maintain the pH near 5.5. Currently, the detection limit achieved in the laboratory is approx. 10 ppm thorium. The methodology can also be applied to uranium determinations and, with necessary modifications, will be used routinely.

The unique feature of this method is that the ion-selective electrode measures the free fluoride ion only. Therefore, if a chelating compound is produced in the culture media in quantity and is able to compete with free fluoride ions for thorium complexation, then an equivalent amount of fluoride ions should be freed and become detectable. Consequently, the presence of thorium chelates can be detected in this multi-chelate system by difference.

EXAMPLE 4

Determination of Thorium in Bacterial Cells

A wet washing method was used for the determination of thorium in washed cells. This method digests the cells in 7 N $HNO_3$ at 80° C. for 24 hr. The acid was then evaporated to dryness at 130° C., and the residue redissolved in distilled water. Samples prepared in this manner were then used in the routine photometric determinations of thorium.

EXAMPLE 5

Determination of Thorium by Radioactivity Counting

For the detection and determination of low concentrations of thorium in thorium chelates which may be produced in a culture media, radioactivity counting methods can be used. Two methods are preferable. In one method, $^{234}$Th-spiked thorium is used and the thorium assay is carried out by means of a well-calibrated Ge(Li) detector for $\gamma$-counting.

The second method of assay involves the use of liquid scintillation alpha-counting. The counter is equipped with both pulse height and pulse shape discrimination schemes which remove the background events such as beta and gamma activity of the sample, sample holder, and photomultiplier tube. Besides the improvement in electronics, the signal is enhanced by using an efficient liquid scintillator, a spherical diffuse-white reflector for the photomultiplier and silicone oil to improve light transmission. With certain improvements in the electronics and the chemistry of sample preparation, extremely low backgrounds are obtainable and the detection limit achievable is about 10 fCi for plutonium.

Either method enables one to assay for thorium well below the picocurie levels.

EXAMPLE 6

Freeze Drying and High Pressure Liquid Chromatography

Ultrafiltration was used for the removal of higher molecular weight fractions (>5,000), and freeze drying was used for the concentration of large samples. Concentrated crude fractions were needed for detailed characterization of new compounds of interest which were being isolated from crude concentrates by preparative column gel permeation chromatography and by high pressure liquid chromatography and related techniques. In the gel permeation chromatography (GPC), a second molecular weight check was carried out. Since the separation by GPC was based on molecular size differences, fractions of specified molecular weight were isolated. All fractionation steps were followed by diagnostic thin layer chromatography.

EXAMPLE 7

Potentiometric Titrations

The titration system consisted of a glass electrode and a titration vessel thermostated at 25.0° C. During titration the solutions were constantly mixed with a magnetic stirrer while $CO_2$-free nitrogen gas saturated with water vapor was passed over the solution. The pH was measured with an Orion 201A digital pH meter calibrated with NBS standard solutions at pH 4.01, 6.86, and 9.18. All solutions used in the titrations were carbonate free, and metal impurities were avoided. The automatic burette functioned by means of a stopper motor which delivers 100% of the volume from a calibrated glass syringe in 10,000 increments. The progress of the titration was monitored by an X-Y recorder. The X-axis was converted to the digital burette via a digital to analog converter, and the Y-axis was directly converted to the pH meter. The titration process was placed under control of a microcomputer. The titration data were automatically stored on magnetic tape for later use in the calculation of formation constants.

EXAMPLE 8

Preparation of Chelating Agents

A twelve liter batch of *P. aeruginosa* strain PAO-1 was grown using a culture medium containing sodium succinate hexahydrate (64.8 g), ammonium chloride (2.57 g), potassium sulfate (2.09 g), magnesium chloride hexahydrate (0.976 g), zinc chloride (1.64 mg), manganese chloride (1.52 mg), buffered with 4 mM potassium phosphate to pH 7.4. In the culture medium containing thorium, 238 mg of $Th(NO_3)_4$ was added to the above constituents. The cultures were centrifuged at maximum growth and the supernatant was filtered through a 0.45 $\mu$m pore diameter membrane, lyophilized and stored at room temperature.

Methanol Extraction: Lyophilized culture medium (5 g) was stirred with 100 ml of absolute $CH_3OH$ at room temperature. The mixture was filtered through a fine sintered glass filter and the filtrate was evaporated to dryness at 40° C. For injection into mice, 0.89 g of NaCl was dissolved in 100 ml of doubly distilled water and the resulting isotonic physiological saline was filtered through a 0.22 $\mu$m pore diameter membrane filter (Millex GS, Millipore).

A similar batch run was performed using *P. aeruginosa CSU* on the organism and the culture medium was concentrated and extracted following the same procedures.

EXAMPLE 9

Thorium Complexes and Uranium Complexes

In order to further explore the nature of substances produced in the presence of thorium or uranium, ultrafiltrates of culture supernatants were fractionated by column chromatography which was followed by thin layer chromatography (see Example 1). Subfractions from column chromatography were pooled according to their approximate molecular weight ranges into three major fractions, A=2000–1000, B=1000–300, and C=<300 daltons respectively. Thin layer chromatography of these fractions and controls, consisting of the autoclaved media containing thorium or uranium with and without supplemental iron, inoculated with *P. aeruginosa*, was carried out as described in Example 1.

Analyses of the chromatograms showed that in absence of supplemental iron there are no thorium complexes present in fraction A and that there are five thorium complexes present in fraction B. One complex was present in the control, leaving four new complexes in the molecular weight range of 1000–300, whose formation in the culture medium during the growth of the microorganism was induced by the presence of thorium. Three of these complexes contained fluorescent groups i.e., isoquinoline, phenol and/or catechol as well as amino and/or hydroxamate components, and one lacked the phenol and/or catechol component. The low molecular weight fraction C contained three complexes of which two were present in the control. The remaining thorium complex was amino and/or hydroxamate positive. There was no thorium detected in three other amino and/or hydroxamate and phenol/catechol positive components of the C fraction. Addition of supplemental iron to the cultures produced a very similar pattern, possibly differing in two components present in trace amounts, in the lower molecular weight fraction.

Identical analyses of uranium complexes showed that in the absence of supplemental iron, fraction A contained two complexes, one with amino and/or hydroxamate and phenol/catechol functions and the other with the phenol/catechol function only. Fraction B contained four complexes, two of which were fluorescent, one contained phenol/catechol functions and amino and/or hydroxamate groups, while the other contained only the phenol/catechol function. The remaining two complexes contained amino and/or hydroxamate functions only. Fraction C, contained three complexes, all fluorescent, two contained phenol/catechol and amino and/or hydroxamate functions and one contained phenol/catechol function only.

In the presence of supplemental iron, fraction A contained three complexes, one present in the control, while the others induced by the presence of uranium were fluorescent, contained amino and/or hydroxamate and phenol/catechol functions. One of these based on the $R_f$ value was different from the complex present in cultures to which supplemental iron was not added. Fraction B contained five complexes, one of which was also present in the control. The remaining complexes, induced by uranium presence, were all fluorescent, contained amino and/or hydroxamate and phenol/catechol functions. Similarly, fraction C contained three fluorescent, amino and/or hydroxamate and phenol/catechol positive complexes.

The distribution of thorium and uranium induced complexes is summarized in Table 2.

High pressure liquid chromatography (HPLC) of maximum growth cultures in absence of thorium, but to which thorium was added prior to analysis and those which were grown in the presence of thorium also confirmed presence of thorium induced microbial products. Mass spectroscopy and nuclear magnetic resonance of HPLC fractions obtained from the maximum growth cultures of P. aeruginosa, grown in the presence of thorium, yielded the following information.

Chromatography of an acidified ethanol extract of PAO-1 thorium culture yielded several fractions containing compounds with molecular weights ranging from 208 to <600 daltons. Fraction containing M/e 209 is consistent with pyrimine $C_{10}N_2O_3H_{12}$ [Shiman et al., Biochemistry, 4 (10), 2233-2236 (1965)], whose identity is further supported by the mass fragmentation pattern of M/e 209, 163, 130, 79, 75, and its PMR spectrum with signals (in ppm) at 3.8, 2.12, 2.33, 8.2, 8.4, 7.5, and 9.04. A fraction containing a compound with molecular weight of M+H+325 with a fragmentation pattern of M/e 325, 223, 220, 219, 191, 178, 146, 137, 120, 102, and 100, is consistent with that reported for a pyochelin, $C_{14}H_{16}N_2O_3S_2$ [Cox et al., Proc. Natl. Acad. Sci. USA, 78 (7), 4256-4260 (1981)]. The PMR spectrum with signals at (in ppm) 9.18, 6.85-7.42, 4.93, 4.42, 3.78, 3.29, and 2.65 further confirms the presence of this compound.

The remaining fractions contain analogues of pyochelin and schizokinen. Preliminary data indicate that at least three fractions contain compounds which do not resemble those reported to be present in *Pseudomonas sp.*

EXAMPLE 10

In vitro Chelation Assay

One gram of mouse liver was homogenized in 5 ml of doubly distilled water using a Teflon/glass ten Broeck tissue grinder at 0° C. The suspension was diluted to a concentration of 1 g wet weight of liver per 40 ml of water and cooled in ice until use. The tests were carried out at ambient room temperature by mixing one volume of the liver suspension with twenty volumes of sample solution (described in Table 3, sample types 1–6, each diluted to 27 ppm thorium with $H_2O$). The mixtures were filtered through a 0.22μm membrane filter and the filtrates analyzed for thorium spectrophotometrically. It was found that within experimental error, all of the thorium in the $Th(NO_3)_4$ preparation (Sample No. 1, Table 3), was adsorbed by the liver, while none was found adsorbed on the 0.22 μm membrane filter. Chelation assay results for the PAO-1 growth media are summarized in Table 3. Samples 2–6 represent duplicate assays of the same growth media. Numbers listed are the arithmetic averages of determinations.

TABLE 2*

| | | Distribution of Thorium and Uranium Induced Complexes | | | | | | | |
|---|---|---|---|---|---|---|---|---|---|
| | | Thorium Complexes | | | | Uranium Complexes | | | |
| Fraction | M.W Range | $R_f$ | <0.05 ppm Iron | $R_f$ | 18 ppm Suppl. Iron | $R_f$ | <0.05 ppm Iron | $R_f$ | 18 ppm Suppl. Iron |
| A | 2000 to 1000 | — | | — | | 0.60 | + | 0.56 | + |
| | | | | | | — | | — | |
| | | | | | | 0.78 | + | 0.78 | + |
| B | 1000 to 300 | 0.53 | + | 0.53 | + | 0.53 | + | 0.49 | + |
| | | 0.62 | + | — | — | 0.62 | + | 0.57 | + |
| | | 0.74 | + | 0.74 | + | 0.71 | + | 0.66 | + |
| | | 0.79 | + | — | — | 0.78 | + | 0.78 | + |
| | | — | | — | — | 0.53 | + | 0.55 | + |
| C | <300 | — | | 0.78 | + | 0.62 | + | 0.62 | + |
| | | 0.78 | + | 0.78 | + | 0.78 | + | 0.78 | + |

*For experimental details see text

| Liver Assay of PAO-1 Extracts | | |
|---|---|---|
| | % Th | |
| Sample Type | Supernatant | Liver |
| 1. $Th(NO_3)_4$, 27 ppm Th | 1 | 99 |
| 2. Thorium succinate, 27 ppm Th | 3 | 97 |
| 3. Culture medium, maximum growth with 27 ppm of Th added immediately prior to the analysis | 9 | 91 |
| 4. Culture medium, maximum growth in the | 98 | 2 |

-continued

Liver Assay of PAO-1 Extracts

| Sample Type | % Th Supernatant | Liver |
|---|---|---|
| presence of 100 ppm Th.* (Thorium concentration prior to analysis adjusted to 27 ppm) | | |
| 5. Culture medium, maximum growth to which Th DTPA was added prior to analysis (≡ 27 ppm Th) | 84 | 6 |
| 6. Culture medium, maximum growth to which Th DFA was added prior to analysis (≡ 27 ppm Th) | 27 | 73 |

*All culture media were centrifuged and ultrafiltered

EXAMPLE 11

In vivo Toxicity Study

For this study four samples were used. These were prepared by dissolving lyophilized culture medium or dried methanolic extract in physiological saline, and filtering through a 0.22 μm pore diameter membrane. The sample concentrations were 10%, 5% and 1% w/v and represented the following extracts:

1. *P. aeruginosa* PAO-1 grown in the absence of thorium
2. *P. aeruginosa* PAO-1 grown in the presence of 100 ppm $Th^{4+}$ added as $Th(NO_3)_4$
3. Methanolic extract of 1
4. Methanolic extract of 2

In vivo study using four 10% solutions in a preliminary test showed that 1 ml injected into the peritoneal cavity of two or three 12-week-old male Hale-Stoner (Brookhaven National Laboratory) Swiss albino mice caused the following effects:

Solution 1: Hyperactivity for about 30 seconds, followed by quiescence, tachypnea, subcostal retraction and weakness. Diarrhea was noted 50 minutes after injection and mice died between 1.5 to 2 hours later.

Solution 2: Similar reaction as to solution 1, but one mouse died 45-90 minutes after injection.

Solution 3: Similar reactions, but mice died 7-10 minutes after injection. Hyperactivity resulted in somersaults.

Solution 4: Some initial reaction, but mice were alive and apparently normal 24 hours after injection. Using twelve 6-week-old male mice these tests were repeated by injecting 1 ml of a 10%, 5% or 1% solution into the peritoneal cavity. These observations are summarized in Table 4.

It would appear that the methanolic extract of the culture medium of the *P. aeruginosa* PAO-1 grown in the presence of 100 ppm thorium as thorium nitrate was non-lethal at the dose of about 100 mg of lyophilized culture medium which sustained maximum bacterial growth, equivalent to about 0.24 liters of the original culture medium. The same quantity of the methanol-extracted lyophylized growth medium from the batch in which the organism was grown to maximal growth in the absence of thorium was rapidly lethal.

TABLE 2

Toxicity Tests
Twelve six weeks old male, Hale-Stoner Swiss albino mice were injected intraperitoneally with 1 ml of a 10%, 5% or 1% test solution

| Test Solution | Mouse Wt (g) | Concentration | Observation After Injection | | |
|---|---|---|---|---|---|
| | | | 1 Min | 20 Min | 24 h |
| 1 | 27 | 10% | hyperactive | tachypnea | dead |
| | 26 | 5% | quiet | piloerection | piloerection tachypnea diarrhea |
| | 24 | 1% | normal | normal | normal |
| 2 | 23 | 10% | hyperactive | tachypnea | dead |
| | 23 | 5% | piloerection | piloerection | piloerection tachypnea diarrhea |
| | 26 | 1% | piloerection | piloerection | piloerection diarrhea |
| 3 | 26 | 10% | hyperactive | dead | — |
| | 25 | 5% | subcostal retraction | subcostal retraction | piloerection normal |
| | 25 | 1% | normal | normal | normal |
| 4 | 25 | 10% | subcostal retraction | diarrhea | normal |
| | 25 | 5% | piloerection | piloerection | normal |
| | 24 | 1% | piloerection | normal | normal |

Solution
1. PAO-1 maximum growth in the absence of thorium.
2. PAO-1 maximum growth in the presence of thorium.
3. $CH_3OH$ extract of 1.
4. $CH_3OH$ extract of 2.

I claim:

1. A mixture of chelating agents that complex with the toxic metal thorium, which agents are produced by the microorganism *Pseudomonas aeroginosa* PAO-1 (ATCC 15692) grown in a conventional growth medium containing thorium as a challenge metal.

2. The mixture of claim 1 produced by growing said microorganism in a medium to which has been added thorium as thorium nitrate.

3. A mixture of chelating agents that complex with the toxic metal uranium, which agents are produced by the microorganism *Pseudomonas aeroginosa* PAO-1 (ATCC 15692) grown in a conventional growth medium containing uranium as a challenge metal.

4. The mixture of claim 3 produced by growing said microorganism in a medium to which has been added uranium as uranyl nitrate.

* * * * *